US006488648B1

(12) United States Patent
Matsugi et al.

(10) Patent No.: US 6,488,648 B1
(45) Date of Patent: Dec. 3, 2002

(54) DEVICE FOR FEEDING A POWDER IN A PREDETERMINED AMOUNT AND METHOD THEREOF

(75) Inventors: Hideo Matsugi, Hino (JP); Yuji Makino, Hino (JP); Masahiko Dohi, Hino (JP); Yasuhide Uejima, Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/646,159

(22) PCT Filed: Jan. 14, 2000

(86) PCT No.: PCT/JP00/00156

§ 371 (c)(1),
(2), (4) Date: Sep. 14, 2000

(87) PCT Pub. No.: WO00/41755

PCT Pub. Date: Jul. 20, 2000

(30) Foreign Application Priority Data

Jan. 14, 1999 (JP) .......................................... 11-007863

(51) Int. Cl.$^7$ ...................... A61M 31/00; A61M 13/00; A61M 15/00; A61M 16/10; B65D 83/06

(52) U.S. Cl. ..................... 604/57; 604/58; 128/203.12; 128/203.15

(58) Field of Search ............................. 604/57, 58, 59, 604/73, 212, 217, 207; 128/203.12, 203.15, 203.19, 203.23

(56) References Cited

U.S. PATENT DOCUMENTS 5,351,683 A * 10/1994 Chiesi et al. .......... 128/203.12
5,549,101 A * 8/1996 Trofast et al. ......... 128/203.15
5,634,900 A * 6/1997 Makino et al. ............... 604/58
5,683,361 A * 11/1997 Elk et al. ....................... 604/58
5,702,362 A * 12/1997 Herold et al. ................. 604/58
6,220,243 B1 * 4/2001 Schaeffer et al. ...... 128/203.15
6,325,061 B1 * 12/2001 Dagsland ............... 128/203.15
6,328,032 B1 * 12/2001 Virtanen ................ 128/203.15

FOREIGN PATENT DOCUMENTS

| | | | |
|---|---|---|---|
| EP | 0 744 188 | 11/1996 | .......... A61M/31/00 |
| JP | 11-33116 | 2/1999 | .......... A61M/13/00 |
| RO | 230751 | 9/1994 | .......... A61M/11/02 |
| RO | 333459 | 6/1998 | .......... A61M/15/08 |
| WO | 94/26338 | 11/1994 | .......... A61M/15/00 |

OTHER PUBLICATIONS

International Search Report.
Patent Abstract of Japan 11033116 Feb. 09, 1999.

* cited by examiner

*Primary Examiner*—William C. Doerrler
(74) *Attorney, Agent, or Firm*—Sughrue Mion, PLLC

(57) ABSTRACT

A powdered medicine multi-dose administering device has a medicine container unit (5*b*) for containing a unit-dose of medicine under the lower surface of the medicine storage chamber (5*a*) storing the medicine in a multi-dose amount. A medicine guiding unit (2) moves between a filling position and an administering position while maintaining a contact with the bottom surface. At the filling position, the medicine container unit is opened to the medicine storage chamber and is filled with the medicine. As the medicine container unit moves from the filling position to the administering position, the powdered medicine in the medicine container unit is swept and metered. At the administering position, the medicine in the medicine container unit is injected by the action of the pump unit (3) through a filter (6) and a pipe (2*g*, 2*d*, 2*c*).

26 Claims, 5 Drawing Sheets

DEVICE FOR FEEDING A POWDER IN A PREDETERMINED AMOUNT AND METHOD THEREOF

TECHNICAL FIELD

The present invention relates to a device for feeding a powder in a predetermined amount and a method thereof. As a typical example, the present invention relates to a multi-dose powdered medicine administering device.

More specifically, the invention relates to a powdered medicine multi-dose administering device by which a powdered medicine of an amount of plural times of administration operations stored in the-device body is extracted and weighed into a unit dose of powdered medicine of a constant quantity, which is a very small amount, and is sprayed.

The invention further provides a relatively inexpensively constructed multi-dose powdered medicine administering device by which a unit dose of powdered medicine can be consecutively and precisely extracted and administered into the body cavity such as the nasal cavity, oral cavity, trachea, bronchus or lung, or into any other diseased part by spraying or inhalation, the device being sanitary, suited to being carried and easy to use.

BACKGROUND ART

Powdered medicine can be administered into a body cavity such as the nasal cavity, oral cavity or airway by means of spraying or inhalation. For example, the powdered medicine is administered by spraying into the nasal cavity of a patient suffering from a nasal allergy, or is administered by inhalation into the air ways of a patient suffering from asthma. For a patient suffering from stomatitis, the powdered medicine is administered by spraying into the oral cavity. Recently, attention has been given to a drug delivery system in which a medicine is absorbed into the bloodstream through the mucous membrane of the nasal cavity or lung, and it has been attempted to administer powdered medicine via a mucous membrane. Peptide/proteinous drugs such as insulin and calcitonin, as well as drugs which must exhibit immediate effect such as migraine-relieving drug and the like drugs have been produced in the form of powdery orally administering agents or inhalable agents that can be conveniently used as substitutes for injected drugs, and it has been frequently reported that such drugs are more favorably absorbed than the orally administered drugs.

To administer the powdered medicine, a powdered medicine administering device is used. Powdered medicine administering devices are roughly classified into one of the two types according to the system for storing the powdered medicine.

In the first type of powdered medicine administering device, a powdered medicine in an amount of a unit-dose administering operation is accommodated in the administering device or in an appropriate container such as a capsule. Therefore, a unit-dose of powdered medicine is administered at each administering operation. This includes those of the disposable type that are discarded after each administering operation.

In the second type of powdered medicine administering devices, a powdered medicine in an amount of many times-of administering operations is accommodated in an appropriate container. Each time an administering operation is carried out, an accurate unit-dose of powdered medicine is extracted from the container and is administered.

In the present invention, the amount of powdered medicine to be administered in a single operation is defined as a "unit-dose", and the amount of powdered medicine to be administered in a plurality of operations. is defined as a "multi-dose".

As an example of the powdered medicine unit-dose administering device, Japanese Unexamined Patent Publication (Kokai) No. 59-34267 discloses one which sprays the powdered medicine into the nasal cavity. In these administering devices, in general, a unit-dose of the powdered medicine is contained in a container such as a capsule, and provision is made of means for piercing the container and air stream introduction means for spraying the powdered medicine from the container into the nasal cavity of a patient. As an example of the disposable unit-dose administering device, International Patent Publication No. 2-500172 discloses an administering device which contains a fine powdery medicine, and includes a holding unit forming an opening in the head portion thereof for spraying the medicine so as to be inhaled, and air introduction means, the bottom of the holding unit being communicated with the air introduction means through an air-permeable diaphragm which does not permit the passage of the medicine. Further, WO 97/04826. discloses an administering device which is an improvement on the above device.

Concerning the unit-dose inhaler by which powdered medicine is inhaled into the air ways, a large number of devices have been proposed. For example, there is provided an inhaler employing capsules that are usually used pharmacologically. In each capsule, a unit-dose of powdered medicine is accommodated. Each administering device is provided with means for piercing the capsule. After the capsule is pierced, the powdered medicine is administered by the air flow created by the inhaling action of the user. The administering devices have their features in the air flow at the time of inhaling and in the state of the capsule. U.S. Pat. Nos. 3,906,950 and 4,013,075 disclose devices in which both ends of the capsule are pierced and the capsule remains stationary during the inhalation, and U.S. Pat. No. 3,807,400 discloses the one in which the capsule moves during the inhalation.

As an example of a multi-dose administering device, the specification of WO 94/26338 (corresponding to U.S. Pat. No. 5,634,900—Makino et al.) discloses one which administers the medicine by spraying. This specification discloses a device comprising a storage chamber detachably attached to the device body and storing multi-dose of medicine, a container chamber having a unit dose capacity, medicine distribution means movably attached to the device body and communicated at the filling position with the storage chamber and with the container chamber to administer the medicine in the container chamber, and pumping means communicated at the filling position with the container chamber to inject air into the storage chamber to stir up the medicine in the storage chamber, wherein the container chamber is filled with a predetermined amount of powdered medicine after stirring as it is transferred from the storage chamber by the sucking force created by the pumping means or by gravity.

As a nasal cavity administering device, European Patent Publication No. 0744188 discloses a nasal cavity applicator comprising a manual air-flow supply source for spraying powdered medicine, a storage chamber for storing multi-dose of powdered medicine, a pipe for passing the powdered medicine, and means for distributing the multi-dose of powdered medicine into a unit doses of powdered medicine. Means for distributing the powdered medicine includes a drum-shaped powdered medicine storage chamber and a rotary sleeve having, on the inside thereof, a plurality of container chambers for containing a unit doses of medicine.

As a device for administering powdered medicine into the air ways by inhalation, European Patent Publication No. 0211595 discloses a device in which a disk-shaped pack is loaded into the device, and a series of bubbles are arranged around the pack under the condition that the distances from the bubbles to the center of the pack are the same. A predetermined quantity (unit-dose) of powdered medicine is accommodated in each bubble. This pack is put on the rotary circular tray about the center axis. The tray has holes at positions corresponding to the bubbles, and when each bubble is moved to a position where it is broken by an appropriate opening device, powdered medicine is taken out from the bubble and is inhaled.

Further, European Patent Publication No. 0069715 discloses the following device. This administering device includes a container, accommodating a predetermined quantity of medicine, and a device for taking out powdered medicine accommodated in the container so as to prepare for the administration of the medicine. The administration preparation device is composed of a plate having a predetermined thickness and a predetermined number of through-holes. The plate is capable of moving from a position at which the through-holes are partly filled with powdered medicine taken out from the container by a mechanical means, to a position at which the holes filled with the medicine are located in the passage. When the user inhales through an inhalation port communicated with the passage, the air enters into the passage, so that the powdered medicine can be taken out from the through-hole. There is provided a scraper, which scrapes the powdered medicine on the container side in the through-hole formed in the plate. According to this specification, the through-holes are completely filled by the action of the scraper. Therefore, a constant dose can be ensured. According to this specification, it is described that the scraper is optionally provided. However, in order to appropriately operate the inhaler, it is necessary to provide the scraper because the doses differ greatly without the scraper. This is because the powdered medicine in many cases has poor fluidity and it frequently occurs that the through-holes are not completely filled with the powdered medicine.

Though many administering devices have heretofore been contrived, they have their problems as described above.

When a unit-dose administering device is compared with a multi-dose administering device, the multi-dose administering device is preferred from the viewpoint of convenience and marketability. This is because, in the case of the unit-dose administering device as disclosed in, for example, Japanese Unexamined Patent Publication (Kokai) No. 59-34267, a container such as capsule is necessary to contain a unit-dose of medicine and, besides, the device must be equipped with means for piercing the container. Therefore, the user must mount the container containing the powdered medicine and must pierce it according to the instruction of the administering device. This is never convenient for the user. The user must carry with him the administering device as well as the container containing the powdered medicine, which is not convenient, either. The specification of WO 97/04826 discloses a device which requires a simplified administering operation. In this case, however, the user who needs a plurality of times of administration must use an administering device containing a plural number of unit-dose medicines, accompanied by a problem from the viewpoint of portability.

The multi-dose administering device is free from the defect related to convenience inherent in the unit-dose administering device but is accompanied by another important problem. That is, it is very difficult to consecutively and quantitatively extract and administer the powdered medicine in an amount necessary for a unit-dose of administration from a large amount of the powdered medicine in a collected form, due to changes in the density of the collected powdered medicine.

Several contrivances have been made to solve the above-mentioned problem. For example, European Patent Publication No. 0069715 mentioned above discloses a method-of continuously filling through-holes of a predetermined capacity with the powdery medicine while holding the hole with a scraper or the like. Even with this method, however, the bulk density of the powdered medicine changes when the administering device as a whole is vibrated, whereby the through-holes of the predetermined amount are filled with varying amounts of the medicine; i.e., the medicine is not administered in a constant amount to the living body. European Patent Publication No. 0744188 discloses means for quantitatively dividing the medicine, i.e., discloses a rotary sleeve equipped with a drum-shaped powdered medicine storage chamber and a container chamber formed on the inside thereof for containing plural unit-dosage medicines. However, the device is relatively complex, uses a large number of parts which are difficult to mold and, hence, is expensive.

Japanese Unexamined Patent Publication (Kokai) No. 3-18376 discloses a multi-dose administering device in which a large quantity of powdered medicine is compressed, and the compressed body of powdered medicine is continuously and quantitatively divided and peeled into pieces. According to this method, the powdered medicine is compressed to ensure a predetermined quantity of the divided medicine. Even with this method, however, when the administering device is vibrated, the bulk density of the compressed powdered medicine changes, resulting in a change in the weight of the compressed powdered medicine that is peeled off. Therefore, the medicine is not administered in a constant amount to the living body. Further, means for uniformly dividing the powdered medicine is relatively complex. To put it into clinical use, therefore, problems are involved such as difficulty in the molding and cost of production.

The specification of WO 94/96338 teaches a multi-dose administering device in which the air- flow passes into the powdered medicine collected in the storage chamber just prior to the dividing operation, the. medicine in the collected form is moved in space in the storage chamber to prevent a change in the density of the powdered medicine and the powdered medicine of an amount of a unit-dose is contained in the powdered medicine container chamber, due to the sucking force and/or gravity, so that the unit-dose of medicine is continuously and quantitatively administered after being divided. However, this device includes a storage unit, a medicine container chamber for containing medicine of a unit-dose, a medicine-metering means and a pumping means and, further, requires a sufficient space for moving the powdered medicine without causing a change in the density. Thus, as the device needs complex parts and is bulky, it is not suited for being carried.

It is desired that the powdered medicine is dispersed into primary particles at a moment when the medicine separates away from the administering device and settles on the administered portion. However, it has been known that the particles cohere during the preservation to form secondary particles; i.e., the particle size distribution shifts toward the larger side. It is therefore desired that even if the powdered medicine is cohered in the administering device during the storage, the powdered medicine is dispersed again into the primary particles at the time when it leaves the administering device.

In a system in which the medicine is divided, in a predetermined volume, into a unit dose in the medicine-containing chamber, the weight of the divided medicine undergoes a change when the bulk density of the powdered medicine changes depending upon the lot number of the medicine. It is therefore desired to adjust the volume of the medicine that is administered depending upon a change in the bulk-density of the medicine.

As described above, none of the conventional powdered medicine administering devices satisfy the requirements of metering the medicine to be administered, providing portability by decreasing the size, easy operability, quick operability, easy production steps, simple constituent parts, low cost of production, and a good dispersing property of the powdered medicine particles.

DISCLOSURE OF THE INVENTION

In view of the above-mentioned problems and assignments of the prior art, the present invention provides a powdered medicine multi-dose administering device that is described below.

That is, the object of the present invention is to provide a powdered medicine multi-dose administering device which satisfies the requirements of spraying the medicine in a predetermined amount, having a small size (portability), an easy and quick operation, an easy production steps, a dispersion of the powdered medicine and a decreased number of parts and low cost.

That is, the present invention is concerned with a powdered medicine multi-dose administering device comprising: means for defining a medicine storage chamber capable of storing a multi-dose amount of powdered medicine; a medicine container unit provided under the bottom surface of said medicine storage chamber and is capable of containing a single-dose amount of powdered medicine; a medicine guiding unit capable of moving between a filling position and an administering position while remaining in contact with the bottom surface of said medicine storage chamber, and, when moved to the filling position, causes said medicine container unit to be opened to said medicine storage chamber through opening means and, when moved to the administering position, causes said medicine container unit to be closed with respect to said medicine storage chamber and causes said medicine container unit to be communicated with the exterior of the device through a pipe; means operated from the outer side of the device to move said medicine guiding unit between the filling position and the administering position; and a pump unit capable of blowing the air into said medicine container unit through a filter provided in the bottom of said medicine container unit; wherein said medicine guiding unit, at the filling position, enables said medicine container unit to be filled with the powdered medicine from said medicine storage chamber through said opening means, sweeps and meters the powdery medicine in said medicine container unit into the amount of one time of administering operation as it moves from the filling position to the administering position, and, at the administering position, permits the powdery medicine in said medicine container unit to be injected out of the device, together with the air, through said pipe when said pump unit is operated.

According to the present invention, the medicine guiding unit can be easily moved upon being operated from the outer side of the device. When the medicine guiding unit is at the filling position, the powdered medicine in the powdered medicine storage chamber falls into the medicine container unit through opening means provided in the medicine guiding unit, and is filled therein. When the medicine guiding unit moves from the filling position to the administering position, the powdered medicine in the medicine container unit is swept and is metered into the amount of one time of administering operation corresponding to the content of the medicine container portion. Thereafter, the medicine container portion is closed. When the medicine guiding portion further moves to arrive at the administering position, the opening of the pipe of the medicine guiding unit comes into match with the medicine container unit. Upon operating the pump unit, therefore, the air is blown into the medicine container unit, and the powdered medicine in the medicine container unit is ejected, together with the air, out of the device through the pipe.

The medicine storage chamber and the medicine container portion are molded integrally together by using a resin to define a body of the device. This makes it possible to simplify the structure of the device body including the medicine storage chamber and the medicine container unit, and to easily produce the device body.

The medicine guiding unit includes a lower disk-like portion and a pole-like portion extending upward from the disk-like portion, which are integrally molded together using a resin, the opening means is so formed as to penetrate vertically through the disk-like portion, and the pipe is opened at its one end on the lower surface of the disk-like portion and is opened at its other end in the upper end of the pole-like portion. The medicine guiding unit is molded as a unitary structure using a resin. Therefore, the opening means and the pipe work to fill and administer the powdered medicine.

The device body is nearly of a cylindrical shape, the disk-like portion of the medicine guiding unit has a diameter smaller than the inner diameter of the medicine storage chamber of the device body, and the medicine guiding unit is allowed to rotate between the filling position and the administering position over a predetermined angular range. Therefore, the medicine guiding unit can be changed over between the filling position and the administering position relying simply upon the rotary operation.

The device body has a closure unit on the medicine storage unit, the closure unit has a shaft hole at the center thereof for passing through the pole-like portion of the medicine guiding unit, and the medicine storage chamber is sealed with the closure unit, medicine storage unit and medicine guiding unit. Thus, the sealing of the medicine storage chamber is maintained, preventing undesired leakage of the powdered medicine.

The bottom surface of the disk-like portion of the medicine guiding unit comes in contact with the bottom surface of the medicine storage chamber, the upper and lower positions of the medicine guiding unit are limited by a contact portion formed on the pole-like portion so as to come into contact with the closure unit, and the bottom surface of the disk-like portion of the medicine guiding unit is brought into intimate contact with the bottom surface of the medicine storage chamber. This maintains an intimate contact between the bottom surface of the disk-like portion of the medicine guiding unit and the bottom surface of the medicine storage chamber, to guarantee correct metering of the powdered medicine and reliable operation.

The medicine guiding unit has a shaft of a circular shape in cross section formed in the upper part of the junction portion of the pole-like portion so as to be fitted to the shaft hole of the closure unit, and has a shaft of a non-circular shape in cross section formed in the upper part thereof, the means operated from the outer side of the device to move the medicine guiding unit between the filling position and the administering position, is a rotary spray metering change-over device which has a non-circular hole that fits to the shaft of a non-circular shape in cross section of the pole portion of the medicine guiding unit, and the medicine guiding unit moves between the filling position and the administering position being interlocked to the rotational operation of the change-over device. By simply rotating the rotary spray metering change-over device from the outside of the device, therefore, the medicine guiding unit can be changed over between the filling position and the administering position, facilitating the operation.

The rotary spray metering change-over device includes a cylindrical portion having a large diameter and a cylindrical portion having a small diameter, that are molded integrally together using a resin, the outer periphery of the cylindrical portion having a large diameter forms a rotary operation portion, and the cylindrical portion of a small diameter defines a powdered medicine passage formed therein, has the non-circular hole formed in the base portion, and defines a spray port in an end thereof. The change-over operation is easily effected by using the cylindrical portion having a large diameter of the change-over device, and the cylindrical portion of a small diameter forms a portion of the powdered medicine passage. Accordingly, the powdered medicine is conveyed up to the spraying port at an end of the device, and is sprayed onto the diseased part.

The rotary spray metering change-over device is formed to be detachable from the device body 1 and the medicine guiding unit. Thus, the change-over device can be removed from the device body and from the medicine guiding unit can be removed from the administering device itself, can be washed and can be easily re-attached to the administering device.

A central hole is formed at the center in the bottom surface of the disk-like portion of the medicine guiding unit, and a protuberance is formed at the center on the bottom surface of the medicine storage chamber to work as a shaft that fits to the central hole in order to stabilize the turning of the medicine guiding unit. Accordingly, the turning of the medicine guiding unit is stabilized, and the rotary spray metering change-over device can be easily turned.

The medicine guiding unit has an arcuate groove formed in the bottom surface of the disk-like portion with the central hole as a center, the medicine storage unit has a protuberance formed on the bottom surface thereof so as to be inserted in the arcuate groove thereby to limit the turning range of the medicine guiding unit and of the rotary spray metering change-over device, wherein, when the protuberance is located at an end of the arcuate groove, the position for filling the powdered medicine is limited and, when the protuberance is located at the other end, the position for administering the powdered medicine is limited.

On the bottom surface of the disk-like portion of the medicine guiding unit, an angle (x) subtended by the center of the opening means and the center of the opening of the pipe is equal to, or is slightly smaller than an angle (y) subtended by one end and other end of the arcuate groove ($x \leqq y$), and lies over a range of from 60 degrees to 180 degrees.

The disk-like portion of the medicine guiding unit on the side of the medicine storage chamber is inclined upward from the periphery toward the center at an angle ($\alpha$) in a range of from 15 degrees to 45 degrees with respect to the bottom surface of the disk-like portion.

The pipe provided in the medicine guiding unit is inclined upward at angles ($\beta$, $\gamma$) in a range of from 20 degrees to 70 degrees with respect to the bottom surface of the medicine guiding unit. The powdered medicine smoothly flows through the pipe at the time when the powdered medicine in the medicine container chamber is injected by operating the pump unit.

The opening means in the medicine guiding unit is a hole penetrating vertically through the disk-like portion.

The hole extends upward from the opening in the bottom surface of the disk-like portion, and expands on the side facing the medicine storage chamber toward the side of the opening of the pipe thereby to form a pocket-like dent, the dent assisting a smooth conveyance of the powdered medicine in the medicine storage chamber into the medicine container chamber during the operation for changing over the filling and administering.

Here, regarding the size of the dent, the medicine can be smoothly conveyed into the medicine container chamber during the operation of the rotary spray metering change-over device when the area of the dent facing the side of the medicine storage chamber is in a range of from 0.1 times to 2.5 times of the opening area and, particularly, from 0.5 times to 1 times of the area of the hole facing the bottom surface of the disk-like portion. As for the depth of the dent, there is no limitation on the depth provided the diameter of the hole remains unchanged on the side of the medicine container chamber. In practice, due to the difficulty in the molding, the depth of the dent is from 10 to 80% and, particularly preferably, 50% of the depth of the hole.

The dent also decreases the thickness of the disk-like portion of the medicine guiding unit. Reduction in the thickness contributes to preventing the contraction or expansion caused by the heat in the medicine guiding unit during the molding, and makesit possible torealize a highly precise spraying performance which is a feature of the powdered medicine multi-dose administering device.

One or plural pieces of vanes are formed on the outer side of the pole-like portion of the medicine guiding unit, so that the powdered medicine in the medicine storage chamber is stirred as the medicine guiding unit moves between the filling position and the administering position.

Here, the vanes possessed by the medicine guiding unit are molded as singe part using the same material as the medicine guiding unit, and may have any shape or thickness provided they can be molded as a single part as described above. The angle subtended by the vanes and the center line of the medicine passage in the guiding unit may lie over a range of from parallel relation, i.e., from 0 degree to 90 degrees but desirably liles in a range of from 0 degree to 45 degrees from the viewpoint of accomplishing a high stirring efficiency of the medicine in the medicine storage chamber during the rotary operation of the,change-over device. When the vanes are provided, it is better that the number of the vanes is two than the number of the vanes is one, since the medicine is more efficiently stirred in the medicine storage chamber due to the rotational operation of the change-over device.

The pump unit is at least partly constituted by a flexible resin so as to define an air chamber therein, the opening portion of the pump unit is coupled to the lower part of the device body, the pump unit is depressed and relaxed to blow the air into the medicine container chamber through the filter in the air chamber, and the powdered medicine is blown out of the device through the pipe.

The filter has a recessed portion or a protruded portion on the side facing the medicine container chamber to adjust the volume of the medicine container chamber. In this case, the size of the recessed portion or of the protruded portion of the filter is changed, and the direction .of the filter is changed, to freely change the volume of the medicine container chamber and to adjust the amount of the powdered medicine administered in one time of administering operation.

The medicine guiding unit is obtained by molding one or more kinds of high-molecular materials selected from the group consisting of a polycarbonate, ABS, a high-impact polystyrene and a cyclic olefin copolymer.

Further, a drying agent is mounted on a portion of the device, the powdered medicine administering device is obtained in a disposable type, and it is realized for administration into the body cavity, into the nasal cavity or into the lung.

BEST MODE FOR CARRYING OUT THE INVENTION

Figure 2:
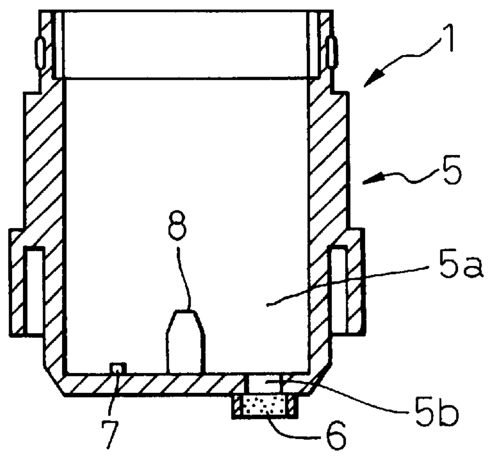
FIG. 2 is a sectional view illustrating a medicine storage unit (5) in a device body (1)
Figure 3:
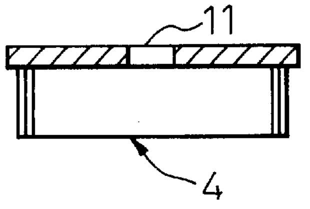
FIG. 3 is a sectional view illustrating a closure unit (4) in the device body (1)
Figure 4:
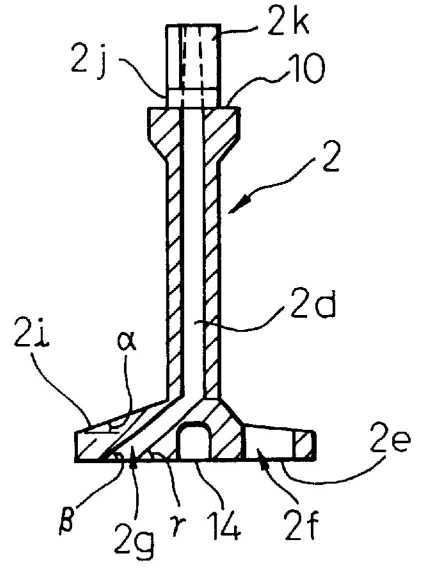
FIG. 4 is a sectional view illustrating a whole medicine guiding unit (2)
Figure 5:
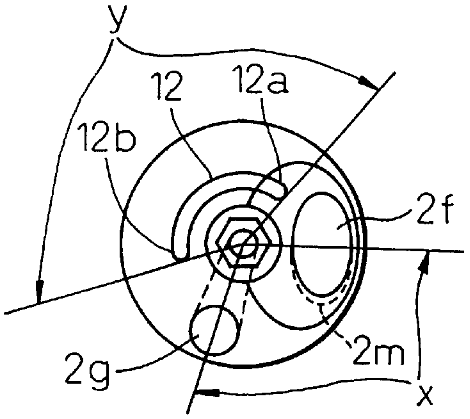
FIG. 5 is a view illustrating the bottom of the medicine guiding unit (2)
Figure 6:
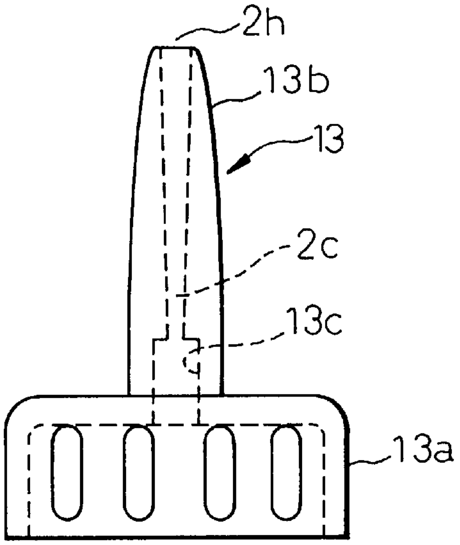
FIG. 6 is a sectional view illustrating a rotary spray metering change-over device (13)
Figure 7:
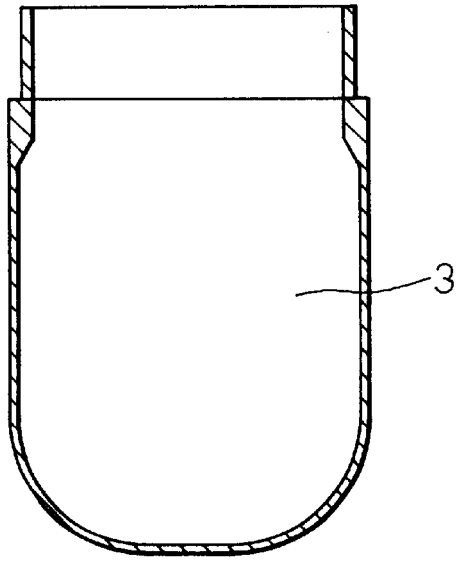
FIG. 7 is a sectional view illustrating a pump unit (3)
Figure 8:
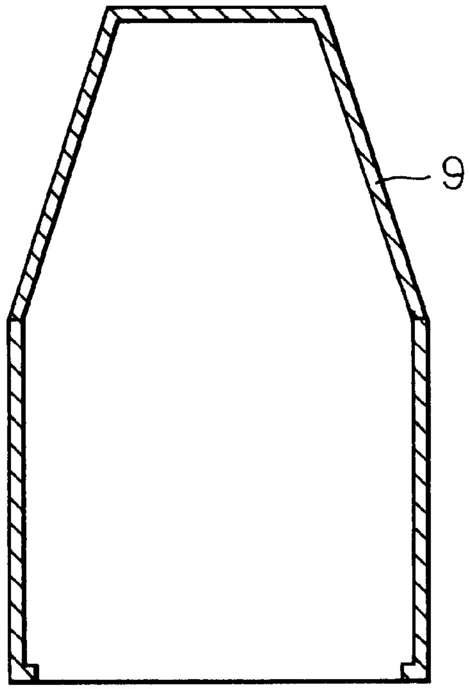
FIG. 8 is a sectional view illustrating a device cover (9)
Figure 10:
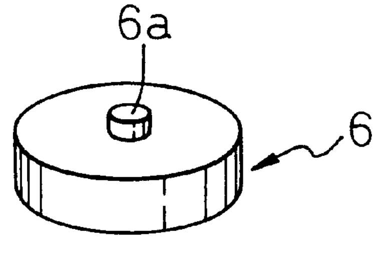
FIG. 10 is a perspective view illustrating an example of the filter (6) provided with a cylindrical protuberance.

The powdered medicine multi-dose administering device (hereinafter often referred to as an administering device) of the present invention comprises:

- a device body (1) constituted by a closure unit (4) shown in FIG. 3 and a medicine storage unit (5) shown in FIG. 2;
- a medicine guiding unit (2) shown in FIG. 4 movably attached to the device body (1);
- a rotary spray metering change-over device (13) shown in FIG. 6 that rotates being interlocked to the medicine guiding unit (2) and has a spray port (2*h*) at an end thereof;
- a pump unit (3) shown in FIG. 7 of which at least a portion of the wall portion that serves as a manual compressed air source for guiding the medicine is constituted by a flexible container or a bag;
- a body cover (9) shown in FIG. 8 for accommodating the spray port (2*h*); and
- a filter (6) shown in FIGS. 2 and 10 for partitioning the medicine container chamber (5*b*), and exhibits the following features (I) to (VI):

(I) The device body (1) is constituted by the closure unit (4) and the medicine storage unit (5), the closure unit (4) having a hole (11) formed at the center thereof for communicating the medicine guiding unit (2) with the device body (1), and the interior of the medicine storage unit (5*a*) is hermetically sealed with the closure unit (4), medicine storage unit (5) and medicine guiding unit (2).

(II) The medicine storage unit (5) has the medicine storage chamber (5*a*) capable of storing the powdered medicine in an amount for administering the medicine many times, and a medicine container chamber (5*b*) formed in the bottom surface of the medicine storage chamber and having a content for administering the powdered medicine one time, the filter (6) being fitted to the bottom surface of the medicine container chamber (5*b*) to permit the passage of the air but inhibiting the passage of the powdered medicine, the filter serving as an air communication port communicated with the pump unit (3) so that the air is blown in upon depressing and releasing the pump unit (3) at the time of guiding the medicine.

(III) The rotary spray metering change-over device (13) having a spray port (2*h*) is interlocked to the medicine guiding unit (2) positioned at the center of the device body so that they rotate together, the rotary spray metering change-over device (13) having, at the center thereof, an air passage (2*c*) for passing the powdered medicine and the air blown out from the pump unit (3) through the medicine container chamber (5*b*) in the device body (1), and capable of being easily detached from the device body (1) and the medicine guiding unit (2) for washing.

(IV) The medicine guiding unit (2) has the passage (2d) for passing the air blown out from the pump unit (3) and for passing the powdered medicine through the medicine container chamber (5*b*) in the device body (1), and the bottom surface (2*e*) of the medicine guiding unit (2) has a disk-like structure of a diameter smaller than the inner diameter of the medicine storage unit (5), the bottom surface (2*e*) separating the medicine storage chamber (5*a*) and the medicine container chamber (5*b*) from each other.

(V) The bottom surface (2*e*) of the medicine guiding unit (2) has, in a portion thereof, a hole (2*f*) of a diameter larger than that of the medicine container chamber (5*b*) for communicating the medicine storage chamber (5*a*) with the medicine container chamber (5*b*), and a pipe (2*g*) for communicating the medicine container chamber (5*b*) with the passage (2*d*) for permitting passage of the powdered medicine and the air blown out from the pump unit (3) through the medicine container chamber (5*b*) in the device body (1).

(VI) The medicine guiding unit (2) is rotated while being linked to the rotary spray metering change-over device (13) to bring the hole (2*f*) in the bottom surface (2*e*) of the medicine guiding unit (2) into agreement with the medicine container chamber (5*b*) in the device body (1), the medicine storage chamber (5*a*) is communicated with the medicine container chamber (5*b*) so that the medicine container chamber (5*b*) is filled with the powdered medicine from the medicine storage chamber (5*a*), and the medicine guiding unit (2) is rotated while being interlocked to the rotary spray metering change-over device (13) whereby the bottom surface (2*e*) of the medicine guiding unit (2) sweeps the powdered medicine in the medicine container chamber (5*b*) so that the powdered medicine, in a predetermined amount, is contained in the medicine container chamber (5*b*). Then the medicine guiding unit (2) is rotated while being interlocked to the rotary spray metering change-over device (13), whereby the medicine container chamber (5*b*), pipe (2*g*), passage (2*d*) and spray port (2*h*) are communicated with one another. The air is blown out from the pump unit (3), and the powdered medicine weighed into a predetermined amount is sprayed from the spray port (2*h*) of the rotary spray metering change-over device (13).

The administering device of the present invention can be assembled in a manner, for example, as described below.

First, the filter (6) is set in position by being pushed from the outer side into the medicine container chamber (5*b*) formed in the bottom on the outer side of the device body (1) (the state shown in FIG. 2). The setting position is defined by forming a step in the medicine container chamber (5*b*) at the time of molding the device body (1). Then, the medicine guiding unit (2) is inserted in the medicine storage unit (5) at such a position that the arcuate groove (12) formed in the bottom surface (2*e*) of the medicine guiding unit is fitted to the protuberance (7) formed on the bottom surface in the medicine storage chamber (5*a*), and the hole (14) at the center of the bottom surface (2*e*) of the medicine guiding unit (2) is fitted and secured to the protuberance (8) at the center of the bottom surface of the device body. Here, the powdered medicine of an amount required for many times of administration operation is introduced into the medicine storage chamber (5*a*) in the device body (1). Then, the closure (4) is intimately adhered and secured to the device body (1) while passing the guiding unit (2) through the hole (11) at the center. Next, the rotary spray metering change-over device (13) having a spray port (2*h*) is secured to the device body (1) in a manner that the end of the guiding unit (2) is brought into agreement with the axis of the rotary spray metering change-over device (13). Next, the pump unit (3) is connected and secured to the lower part of the device body (1) and, finally, the body cover is connected to the device body (1) so as to cover the spray port (2*h*) to thereby complete the administering device of the invention.

Next, described below are the materials constituting the parts of the present invention.

It is desired that the device body (1), medicine guiding unit (2) rotary spray metering change-over device (13), closure (4) and body cover (9) are usually obtained by molding one or more kinds of polymers selected from the group consisting of polyethylene, polystyrene, polypropylene, styrene/acrylonitrile polymer (AS), acrylonitrile/butadiene/styrene polymer (ASS), polycarbonate, high-impact polystyrene and cyclic polyolefin copolymer, to which, however, they are in no way limited.

Among them, it is desired that. the medicine guiding unit (2) is obtained by molding one or more polymers selected from the group consisting of acrylonitrile/butadiene/styrene polymer (ABS), polycarbonate, high-impact polystyrene and cyclic polyolefin copolymer in order to increase the intimate adhesion between the medicine guiding unit (2) and the device body (1).

As the filter (6) provided at an end of the medicine container chamber (5*b*) of the invention; there can be suitably used a sieving mesh or a membrane filter depending upon the size of particles of the medicine and the excipient (which may not always be used) constituting the-powdered medicine. When used for spraying the medicine into the nasal cavity, there is used a membrane filter or a sieving mesh having a size of openings of not larger than 50 $\mu$m with a porous diameter of, preferably, from 0.5 to 38 $\mu$m and, more preferably, from 1 to 25 $\mu$m. When used for spraying the medicine into the air ways, there is used a membrane filter having a size of openings of not larger than 1 $\mu$m. The sieving mesh may be made of a nylon or a stainless steel, and the membrane filter may be made of a polyethylene, polypropylene, cotton, rayon, glass fiber or may be a sintered filter.

The pump unit (3) of the invention is an element for compressing the air to administer the powdered medicine (by spraying or inhalation). It is desired that at least a portion of the flexible member or of the wall of the pump is made of a flexible material. Here, at least a portion is made of a flexible material means that upon pushing and relaxing a portion made of the flexible material, the powdered medicine contained in the medicine container chamber (5*b*) can be sprayed or inhaled. This includes the cases where the whole pump unit (3) is constituted by the flexible material, and where the pump unit (3) is constituted by the flexible material except a portion near the junction portion to the device body (1) and other portions are constituted by the non-flexible material.

As such a flexible material, there can be used an plastic having elasticity such as polyethylene or polypropylene, and a natural or a synthetic rubber.

The powdered medicine used in the present invention can be constituted by, for example, a medicine and a widely known excipient such as milk sugar, starches, celluloses or polyvinyl polymer, or may be constituted by a medicine alone. As required, further, the powdered medicine may be suitably blended with known additives such as stabilizers, antioxidants or the like.

As the medicine to be used for the invention, there can be used a wide range of medicines. Concrete examples include non-peptide/proteinaceous drugs such as steroidal anti-inflammatory drugs or non steroidal anti-inflammatory drugs, analgesics anti-inflammatory drugs, antimuscarinics, antidepressants, cough suppressants expectorants mucolytics, anti-histamic agents, anti-allergic agents, nausea-suppressing agents, anti-insomnia drugs, vitamins, sex hormones, anti-neoplastics, anti-arrhythmias, hypertension drugs, anxyiolytic sedatives, anti-psychotics, anti gastric ulcer drugs, heart failure treating drugs, analgesics, bronchodilators, obesity treating agents, platelet coaggregation suppressing agents, anti-diabetics, muscle-relaxants, anti-migraines, and anti-rheumatoid arthritis drugs. There can be further used peptide/proteinaceous drugs such as hormones, cytokins, vaccines, as well as nuclear acids such as anti-sense and genes.

As the non-peptide/proteinaceous medicines, there can be used those of one or two or more kinds of the drugs are selected from the above-mentioned group. Among them, there can be preferably selected one or two or more of those selected from the group consisting of nausea-suppressing agents, anti-insomnia drugs vitamins, sex hormones, anti-migraines and analgesics.

As the non-peptide/proteinaceous drug, there can be exemplified one or two or more kinds of non-peptide/proteinaceous drugs selected from the group consisting of steroidal anti-inflammatory drugs or non steroidal anti-inflammatory drugs, such as hydrocortisone, predonisolone, triamcinolone, dexamethasone, betamethasone, becromethasone, fluticasone, momethasone, fluocortine, budesonide, salbutamol, salmeterol; analgesics anti-inflammatory drugs such as acetaminophen, phenacetin, aspirin, aminopirin, sulpirin, phenylbutazone, mefenamic acid, fulfenamic acid, ibufenac, ibuprofen, alchlofenac, dichlofenac and indomethacin; antimuscarinics such as scopolamine; antidepressants such as imipramine; cough suppressants expectorants mucolytics such as sodium chlomoglicate, codeine phosphate and isoproterenol hydrochloride; anti-histamic agents such as diphenhydramine, triprolydine, isothipendyl, and chlorophenylamine; anti-allergic agents such as amlexanox, azelastin, ozagrel, tranilast and ketotifen; nausea-suppressing drugs such as ondansetron, granisetron, metoclopramide, cisapride, domperidone; anti-insomnia drugs such as brotizolam and melatonin; vitamins such as cyanocobalamin, mecobalamin; sex hormones such as estradiol, estriol, progesterone, and testosterone; anti-neoplastics such as tamoxifen and tegafur; anti arrhythmias such as proplanolol, atenolol; hypertension drugs such as nicardipine; anxyiolytic sedatives such as diazepam; anti-psychotics such as nitrazepam; anti gastric ulcer drugs such as cimetidine and ranitidine; heart failure treating drugs such as dopamine; analgesics such as morphine and buprenorphine; bronchodilators such as oxytropium and ozagrel; obesity-treating drugs such as mazindol; platelet coaggregation suppressing agents such as beraprost and carbacyclin; anti-diabetics such as acarbose and; muscle relaxants such as pinaberium and inaperizon; anti-migraines such as ergotamine, imigran and alniditan; and anti-rheumatoid arthritis drugs such as actarit and platonin.

As the peptide/proteinaceous drugs, there can be exemplified hormones and cytocains such as lutenising hormone-releasing hormones, growth hormone-releasing factors, somatostatin derivatives, vasopressins, oxytocins, hirudin derivatives, enkephalins, adrenocorticotropic hormone derivatives, bradikinin derivatives, carcitonins, insulins, glucagon derivatives, growth hormones, growth hormone-releasing hormones, lutenising hormones, insuline-growing factors, carcitonin gene-related peptides, atrium sodium urination peptide derivatives, parathyroid hormones, parathyroid hormone-releasing hormones, prolactin, thyroid stimulating hormone-releasing hormones, angiotensins, interferons, interleukins, erythropoietin, granulocyte colony stimulating factor, and macrophage formation-stimulating factor. As the peptide/protenaceous drugs, those selected from the above-mentioned group can be used in one, two or more kinds.

As the vaccines, there can be exemplified whooping cough vaccine, diphtheria vaccine and influenza vaccine.

Described below are the sizes and volumes of the constituent parts of the invention.

The medicine storage unit (5) which is an internal space of the device body (1) of the invention has a volume as small as possible to offer good operability. More specifically, they are determined by the protuberances (7 and 8) on the bottom surface in the medicine storage unit (5), sizes of the opening of the medicine container chamber **(5*b*) and of the medicine guiding unit (2), size of the pump unit (3) to be connected and the method of its connection, size of the operating portion of the rotary spray metering change-over device (13) (portion for turning the rotary spray metering change-over device (13)** by hand) and the amount of the medicine that is stored.

The amount of the medicine to be stored in the administering device of the invention varies depending upon the kind of the medicine. When, for example, the powdered medicine is to be administered into the two nasal cavities two times a day in an amount of 15 mg each time per one cavity (i.e., four times a day), then, the amount (weight) of the powdered medicine to be stored for two weeks use becomes 15×4×14=840 mg. If the powdered medicine has a bulk density of 0.6, then, the volume is 1.4 ml. Therefore, if the device body (1) has a depth of 25 mm and a diameter of 16 mm to maintain a volume of about 5 ml, then, there is realized a small administering device capable of storing the medicine in a sufficient amount even by taking the junction portion (10) between the medicine guiding unit (2) contained therein and the closure unit (4) into consideration.

Further, the volume of the medicine container chamber **(5*b*) in the device body (1) can be suitably determined depending upon the volume of the powdered medicine used in each administering operation and the number of times of administering operation. When the powdered medicine that is usually used has an apparent specific gravity of about 0.1 to 3.0 and the powdered medicine is used in an amount of about 5 to 200 mg each time, then, the medicine container chamber (5*b*)** must have a volume of about 2 to 2000 $mm^3$.

Figure 9:
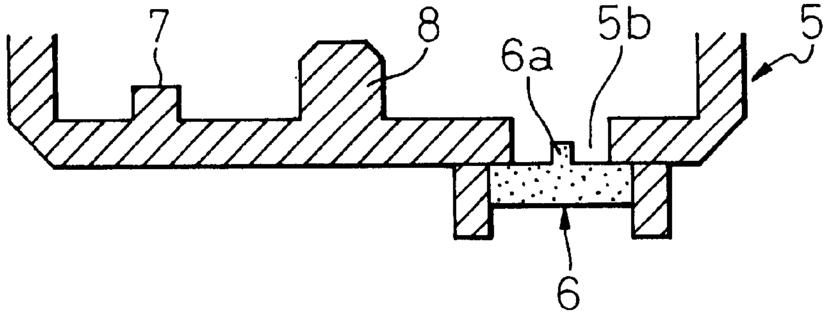
FIG. 9 is a sectional view illustrating a medicine container chamber (5*b*) inclusive of a filter (6) provided with a cylindrical protuberance.

The volume of the medicine container chamber **(5*b*) can be adjusted by providing the filter (6) with a recessed portion or a protruded portion of a dissimilar volume. By adjusting the volume of the recessed portion or the protruded portion depending upon the bulk density of the powdered medicine, it is possible to adjust the weight of the medicine that is metered and picked up depending upon a change in the bulk density of the powdered medicine. Though there is no particular limitation in the shape of the recessed portion or in the protruded portion, there can be exemplified a cylindrical shape, a conical shape or a semispherical shape. In the example shown in FIGS. 9 and 10, the protuberance 6*a* formed on the filter (6)** is of a cylindrical shape.

It is desired that the pump unit (3) of the invention is capable of blowing the air in such amounts that the powdered medicine contained in the medicine container chamber **(5*b*) is almost all discharged upon depressing the pump unit (3)** one to ten times.

The invention will be described in further detail.

According to the administering device of the invention, the medicine in the medicine storage chamber **(5*a*) is contained in the medicine container chamber (5*b*) by turning the medicine guiding unit (2) being interlocked to the rotary spray metering change-over device (13), the unit-dose of medicine is swept by turning the medicine guiding unit (2) in the reverse direction so as to be contained in the medicine container chamber (b). Thus, the unit-dose of medicine can be easily and correctly picked up and metered from the powdered medicine of a multi-dose amount stored in the medicine storage chamber (5*a*)** without using any particular device such as scraper and without using any means for preventing a change in the density by passing air to cope with a change or deviation in the bulk density of the powdered medicine that may occur during the preservation.

Here;

(a) since the closure unit (4) is mounted on the device body (1), the medicine guiding unit (2) is brought into intimate contact with the medicine storage chamber (5*a*) and no medicine leaks through the gap between the medicine guiding unit (2) and the medicine storage chamber (5*a*) and, besides, the powdered medicine does not change its physical properties because the interior of the medicine storage chamber (5*a*) is hermetically sealed;

(b) the medicine guiding unit (2) is turned in an intimately adhered state mentioned in (a) above involving a slight degree of resistance to impart a suitable degree of vibration to the powdered medicine and to prevent a change in the density of the powdered medicine;

(c) the hole (2*f*) formed in the bottom surface (2*e*) of the medicine guiding unit (2) for connecting the medicine storage chamber (5*a*) with the medicine container chamber (5*b*), has a diameter larger than that of the medicine container chamber (5*b*), enabling the medicine to be reliably contained in the medicine container chamber (5*b*); and (d) the surface (2*i*) of the medicine guiding unit (2) on the side of the medicine storage chamber (5*a*) is inclined by an angle (α) relative to the bottom surface (2*e*) of the medicine guiding unit (2) to impart suitable degree of vibration and motion to the powder to increase its fluidity when the medicine guiding unit (2) rotates, so that the medicine is reliably contained in the medicine container chamber (5*b*);

thus making it possible to make uniform the amount of the powdered medicine contained in the medicine container chamber (5*b*).

In the administering device of the invention, a decrease in the number of the parts contributes to minimizing the size of the whole device. Besides, the passage (2*d*) that is installed along the axis of the medicine guiding unit (2) contributes to minimizing the size (height) of the administering device as a whole, so that it can be easily carried.

The administering device of the present invention has the arcuate groove (12) formed in the bottom surface (2*e*) of the medicine guiding unit (2), has the protuberance (7) formed on the bottom surface in the medicine storage chamber (5*a*) to be inserted in the groove (12), permits the rotary spray metering change-over device (13) to be turned due to the above engagement, enables the hole (2*f*) in the bottom surface (2*e*) of the medicine guiding unit (2) to be superposed on the medicine container chamber (5*b*) of the device body (1) when the protuberance (7) arrives at the extreme end of the groove (12) so that the medicine container chamber (5*b*) is filled with the powdered medicine, and enables the pipe (2*g*) of the medicine guiding unit (2) to be connected to the medicine container chamber (5*b*) when the protuberance arrives at the extreme end of the groove (12) on the opposite side so that the powdered medicine in the medicine container chamber (5*b*) is ready to be sprayed. When a charging position is marked at an end of the turn of the rotary spray metering change-over device (13) where the medicine is filled and the other end is marked as a spraying position, then, the device can be more easily operated while preventing erroneous operation.

By imparting a click mechanism to the arcuate groove (12) or to the protuberance (7) inserted in the groove (12) so that both ends of the groove (12) can be confirmed, it is possible to easily perceive the filling position and the spraying position. A suitable degree of vibration, produced at the time of manipulating the click mechanism, imparts a suitable degree of vibration and motion to the powdered medicine so as to increase the fluidity, so that the medicine is reliably contained in the medicine container chamber (5*b*) to improve the metering performance.

It is desired that the angle (x) subtended by the center of the pipe (2*g*) and the center of the hole (2*f*) formed in the bottom surface (2*e*) of the medicine guiding unit (2) and having a diameter larger than the medicine container chamber (5*b*) for communicating the medicine storage unit (5*a*) with the medicine container chamber (5*b*), is equal to, or is slightly larger than, the angle (y) of the arcuate groove (12) ($x \leqq y$), and is in a range of from 60 degrees to 180 degrees and, more preferably, from about 90 degrees to 120 degrees.

It is desired that the surface (2*i*) of the medicine guiding unit (2) on the side of the medicine storage chamber (5*a*) is inclined downward from the center toward the periphery at an angle (α) of 15 degrees to 45 degrees with respect to the bottom surface (2*e*) of the medicine guiding unit (2) from the standpoint of metering the medicine. More preferably, thesurface (2*i*) is inclined at an angle of 25 degrees to 35 degrees. It is further desired that the pipe (2*g*) of the medicine guiding unit (2) has a cross sectional area which gradually decreases upward from the bottom portion, and is inclined at angles (β, γ) of in a range of from 20 degrees to 60 degrees with respect to the bottom surface (2*e*) of the medicine guiding unit (2) from the standpoint of dispersing the medicine. The angle (β) is that of inner wall of the pipe (2*g*) on the peripheral side of the medicine guiding unit (2) and the angle (γ) is that of the inner wall of the pipe (2*g*) on the inner side. More preferably, the angles (β, γ) are in a range of from 25 degrees to 40 degrees.

The administering device of the invention may be furnished with a drying agent that is usually used to avoid a change in the bulk density of the powdered medicine caused by humidity and to maintain the dispersing property of the medicine when it is sprayed.

The administering device of the present invention may be disposable.

Though there is no particular limitation on the portions to where the powdered medicine can be administered by using the administering device of the invention, the medicine can be administered into body cavities such as a nasal cavity or the lungs.

The invention will now be described by way of examples with reference to the accompanying drawings. It should, however, be noted that the invention is in no way limited thereto.

EXAMPLE 1

Figure 1:
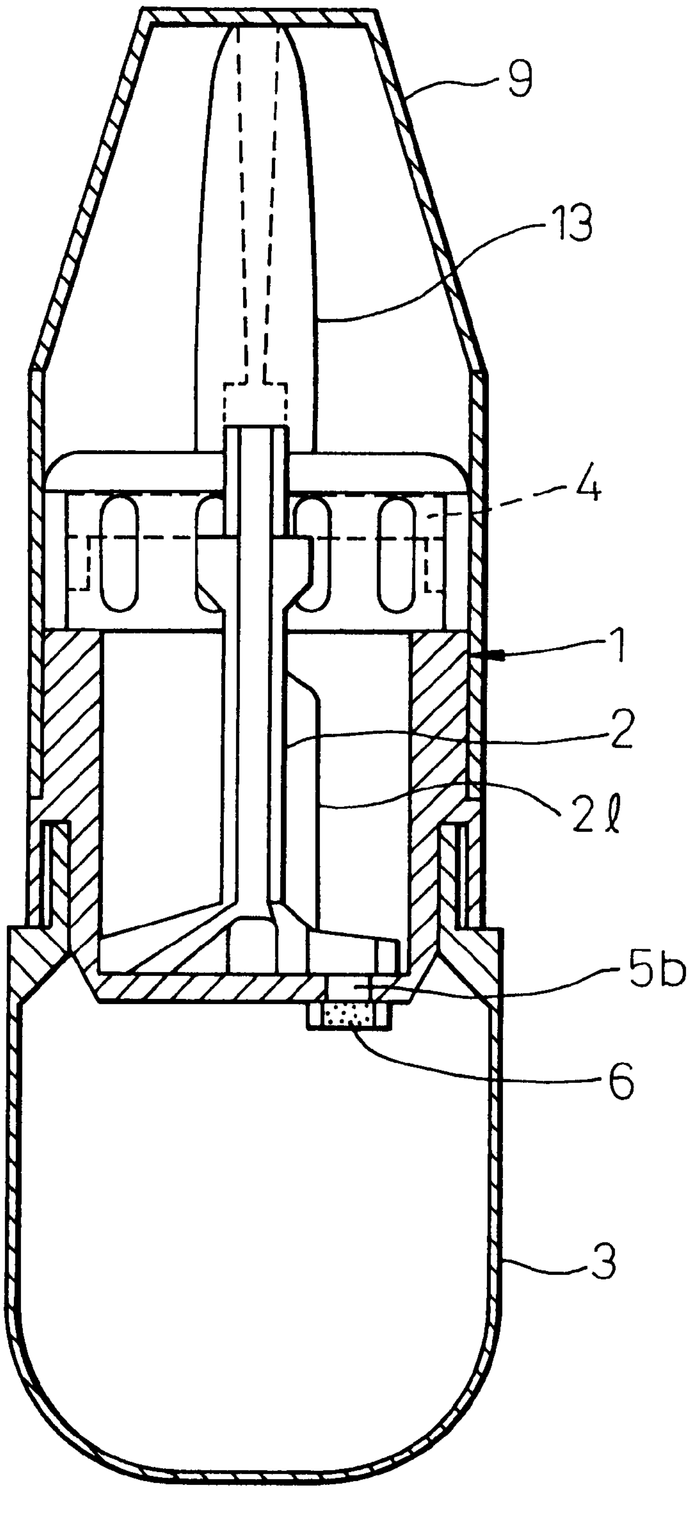
FIG. 1 is a sectional view illustrating a powdered medicine multi-dose administering device according to an embodiment of the present invention.

FIG. 1 is a sectional view illustrating the entire constitution of the multi-dose powdered medicine administering device according to the present invention.

The device body (1) of a cylindrical shape shown in FIG. 2 was obtained by molding a cyclic olefin copolymer, the device body (1) having a medicine storage chamber (5) of an inner diameter of 15 mm and having a medicine container chamber (5*b*) of a diameter of 3.5 mm and a depth of 3.3 mm. Further, the rotary spray metering change-over device (13) shown in FIG. 6 was obtained by molding polypropylene, the rotary spray metering change-over device (13) having a spray port (2*h*) of a diameter of 4 mm and having a bottom portion of an inner diameter of 18 mm for connecting the closure unit (4) to the device body (1). The medicine guiding unit (2) shown in FIG. 4 was obtained by molding a cyclic olefin copolymer and was mounted on the device body, the medicine guiding unit (2) having the shape of a disk with a bottom surface of a diameter of 15 mm and a pole of a height of 27.5 mm connected to the rotary spray metering change-over device (13). In the medicine guiding unit (2), the angle (γ) of the groove (12) formed in the bottom surface (2*e*) and the angle (x) subtended by the center of the hole (2*f*) and the center of the pipe (2*g*), were set to be 115 degrees, respectively. The angle (α) of the surface (2*i*) to the bottom surface (2*e*) was 30 degrees, and the angles of the pipe (2*g*) were 35 degrees (β) with respect to the bottom surface (2*e*) on the outer side and 40 degrees (γ) with respect to the bottom surface (2*e*) on the inner side. The closure unit (4) shown in FIG. 3 was obtained by molding a polyropylene, the closure unit (4) having a hole (11) of a diameter of 5.0 mm in which an end (10) of the medicine guiding unit (2) was inserted. Next, the device body (1) was equipped with a membrane filter (6) made of a polypropylene having an opening size of 5 μm and with a pump unit (3) made of polyethylene. The medicine storage unit (5) was filled with 1000 mg of the powdered medicine having a particle diameter of 38 to 150 μm. The closure unit (4) was inserted in the device body (1), the rotary spray metering change-over device (13) was mounted on the main body (1) and, finally, the spray port (2*h*) was covered with a device cover (9) made of polypropylene to complete the administering device of the invention (the whole device having a height of about 85 mm and a diameter of about 24 mm).

COMPARATIVE EXAMPLE 1

In Example 1, the device body (1) and the medicine guiding unit (2) were obtained by molding a cyclic olefin copolymer. In Control Example 1, however, these two parts were obtained by molding a polypropylene. One gram of a mixture powder (bulk density=0.50) of a hydroxypropyl cellulose (99.8%) having a particle size of 49 to 150 microns and magnesium stearate (0.2%) was introduced into the medicine storage units (5) of these Examples 1 and Comparative Examples 1. The rotary spray metering change-over device (13) was reciprocally moved between the filling position and the spraying position, and the pump was depressed at the spraying position to consecutively spray the mixture powder. The total weight of the administering device was measured each time to record the spraying amount of unit-dose. After sprayed 30 times, Example 1 offered a very stable and constant spraying amount of 16.7 mg (CV=2.2%) in average, and permitted the rotary spray metering change-over device (13) to smoothly rotate reciprocally without any problem. In the Comparative Example, the spraying amount was 16.0 mg (CV 2.8%) in average which was as uniform as that of Example 1. After about twentieth administering operation, however, resistance was involved in the reciprocal motion of the rotary spray metering change-over device (13). When left to stand one day after the thirtieth administering operation, the rotary spray metering change-over device (13) hardly rotated. Further, the mixture powder was found between the bottom surface in the device body and the medicine guiding unit (2). From this fact, it was presumed that an error was occurring in the sizes of the device body (1) and in the medicine guiding unit (2) of Comparative Example 1 due to the high-molecular material used for the molding.

EXAMPLES 2 TO 4 AND COMPARATIVE EXAMPLE 2

In Examples 2 to 4, the administering devices were produced in the same manner as in Example 1 but forming the device body (1) and the medicine guiding unit (2) by molding polycarbonate, ABS and high-impact polystyrene. In Example 2, the administering device was produced in the same manner as in Example 1 but forming the main body (1) and the medicine guiding unit (2) by molding a polyethylene. These four kinds of administering devices were tested in the same manner as described in Comparative Example 1. Comparative Example 2 exhibited the same results as Comparative Example 1, and Examples 2 to 4 exhibited nearly the same results as Example 1.

EXAMPLES 5, 6 AND COMPARATIVE EXAMPLES 3, 4

The administering devices of Examples 5 and 6 in which the angle α was changed from 0 degree to 50 degree while maintaining the angles β and γ at 35 and 40 degrees, and the administering devices of Control Examples 3 and 4 (see Table 1) were subjected to the same spraying test as that of Example 1. The results were as shown in Table 1. It was learned that a favorable spraying performance is exhibited when the angle lies within a range of from 15 to 45 degrees.

TABLE 1

Effect of the medicine guiding units having dissimilar angles α upon the powdered medicine spraying performance.

Figure 11:
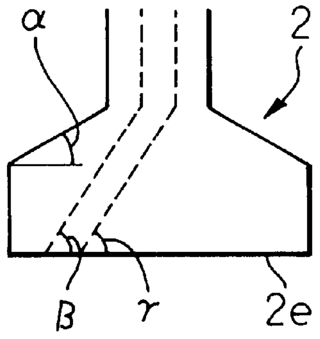
FIG. 11 is a view illustrating near the bottom surface of the medicine guiding unit (2) and shows an angle of a pipe (2*g*)
Figure 13:
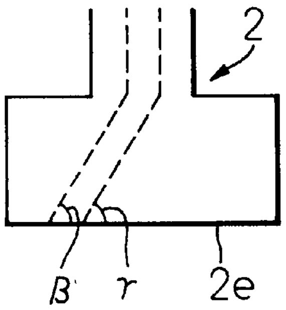
FIG. 13 is a view illustrating near the bottom surface of the medicine guiding unit (2) and where the direction of the pipe (2*g*) is changed

| | Corresponding figure | Angle α (°) | Angle β (°) | Angle γ (°) | Ave. spraying amount (mg) | CV* (%) | Max. | Min. |
|---|---|---|---|---|---|---|---|---|
| Ex. 1 | FIG. 11 | 30 | 35 | 40 | 16.7 | 2.2 | 17.1 | 14.8 |
| Ex. 5 | FIG. 11 | 15 | 35 | 40 | 16.9 | 2.8 | 17.4 | 14.7 |
| Ex. 6 | FIG. 11 | 45 | 35 | 40 | 16.8 | 2.5 | 17.5 | 15.0 |
| Comp. Ex. 3 | FIG. 13 | 0 | 35 | 40 | 15.8 | 8.7 | 17.5 | 11.3 |
| Comp. Ex. 4 | FIG. 11 | 50 | 35 | 40 | 14.9 | 7.5 | 18.0 | 10.3 |

CV*: Fluctuation coefficient = standard deviation/ave. value

EXAMPLES 7 TO 9 AND COMPARATIVE EXAMPLES 5 TO 7

The administering devices of Examples 7 to 9 in which the angles β and γ were changed from 15 degree to 90 degree while maintaining the angle α at 30 degrees, and the administering devices of Control Examples 5 to 7 (see Table 2) were measured for their amounts sprayed in one time of administering operation and particle size distributions of the powdered medicine sprayed through the spray port (2*h*) by using a laser diffraction particle size distribution measuring instrument to find segments (cohered masses) of a particle diameter of not smaller than 300 microns. The results were as shown in Table 2. In Comparative Examples 5 and 7, the spraying amounts were decreased and in Comparative Example 6, the dispersing property of the particles was deteriorated.

TABLE 2

Effect of the medicine guiding units having dissimilar angles β and γ upon the powdered medicine dispersing performance.

Figure 12:
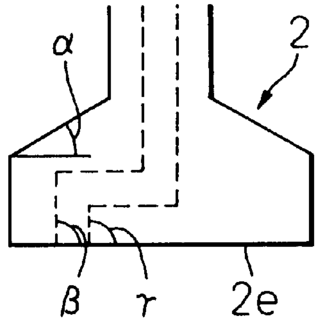
FIG. 12 is a view illustrating near the bottom surface of the medicine guiding unit (2) and where the direction of the pipe (2*g*) is changed.

| | Corre-sponding figure | Angle α (°) | Angle β (°) | Angle γ (°) | Ave. spraying amount (mg) | Segments larger than 300 μm (%) |
|---|---|---|---|---|---|---|
| Ex. 1 | FIG. 11 | 30 | 35 | 40 | 16.7 | 5.0 |
| Ex. 7 | FIG. 11 | 30 | 60 | 60 | 16.8 | 7.0 |
| Ex. 8 | FIG. 11 | 30 | 20 | 20 | 16.6 | 4.7 |
| Ex. 9 | FIG. 11 | 30 | 70 | 70 | 16.8 | 6.8 |
| Comp. Ex. 5 | FIG. 12 | 30 | 90 | 90 | 13.0 | 7.3 |
| Comp. Ex. 6 | FIG. 11 | 30 | 75 | 75 | 16.8 | 13.2 |
| Comp. Ex. 7 | FIG. 11 | 30 | 15 | 15 | 13.5 | 7.8 |

EXAMPLES 10 TO 13

Controlling the unit-dose spraying amount by forming dents and protuberances in the filter (6).

A filter A having a volume of 0.00335 $cm^3$ on the front side (convex surface) and having a flat back surface (without a recess or a protuberance) and a filter B having a volume of 0.00670 $cm^3$ on the font side (convex surface) and having a volume of 0.00335 $cm^3$ in the back surface (concave surface) were adhered on their front surfaces and back surfaces to the medicine multi-dose administering devices of the invention having a medicine container chamber (5*b*) of a volume of 0.0314 $cm^3$, and the powdered medicine spraying testing was conducted. That is, when the front surface of the filter A faced the medicine container chamber (5*b*) (Example 10), the volume of the container chamber was 0.0314–0.00335=0.02805 $cm^3$. Similarly, when the back surface of the filter A faced the medicine container chamber (5*b*) (Example 11), the volume-of the container chamber was 0.0314 $cm^3$ and when the surface of the filter B faced the medicine container chamber (5*b*) (Example 12), the volume of the container chamber was 0.0314–0.00670=0.02470 $cm^3$. Similarly, when the back surface of the filter B faced the medicine container chamber (Example 13), the volume of the container chamber was 0.0314+0.00335=0.03475 $cm^3$.

In these cases, the medicine storage chambers were each filled with 650 mg of the powdered medicine. The powdered medicine was sprayed with n=6. The average spraying amounts and CV% were as shown in Table 3.

TABLE 3

Average spraying amounts and CV % depending upon dents and protuberances of the filter (6).

| | | | | | | |
|---|---|---|---|---|---|---|
| Powder lot No. | 88041 | 88042 | 88051 | 8A121 | 8A151 | 96281 |
| Low bulk density | 0.456 | 0.441 | 0.493 | 0.441 | 0.525 | 0.442 |
| High bulk density | 0.570 | 0.553 | 0.606 | 0.555 | 0.645 | 0.553 |
| Ex. 10 | 13.38 (0.25%) | 12.60 (1.34%) | 12.98 (0.98%) | 12.94 (2.72%) | 13.52 (1.48%) | 10.56 (1.91%) |

TABLE 3-continued

Average spraying amounts and CV % depending upon dents and protuberances of the filter (6).

| | | | | | | |
|---|---|---|---|---|---|---|
| Ex. 11 | 15.12 (2.11%) | 14.72 (0.92%) | 15.82 (1.48%) | 14.92 (1.86%) | 16.44 (2.25%) | 13.56 (1.72%) |
| Ex. 12 | 9.76 (0.85%) | 9.82 (1.43%) | 10.44 (2.19%) | 10.26 (3.12%) | 10.70 (2.53%) | 8.16 (1.83%) |
| Ex. 13 | 16.74 (0.91%) | 16.26 (1.88%) | 16.92 (1.41%) | 16.70 (2.36%) | 18.30 (0.81%) | 15.42 (1.92%) |

INDUSTRIAL APPLICABILITY

The present invention provides a relatively inexpensively constructed powdered medicine multi-dose administering device which is convenient to carry, easy to use, and is capable of correctly administering the powdered medicine in a predetermined amount by spraying or inhalation, which is an excellent effect.

The invention is adapted as an administering device containing, in the container, multi-dose amount of the powdered medicine which is administered in a very small amount in each administering operation.

What is claimed is:

1. A powdered medicine multi-dose administering device comprising:

means for defining a stationary medicine storage chamber (5*a*) capable of storing a multi-dose amount of powdered medicine;

a stationary medicine container unit (5*b*), formed integrally with said medicine storage chamber (5*a*) to form a unitary body (1) of the device, provided under the bottom surface of said medicine storage chamber (5*a*), and capable of containing a single-dose amount of powdered medicine;

a movable medicine guiding unit (2) capable of moving between a filling position and an administering position while maintaining contact with the bottom surface of said medicine storage chamber (5*a*), and, when moved to the filling position, causes said medicine container unit (5*b*) to be opened to said medicine storage chamber (5*a*) through opening means (2*f*) and, when moved to the administering position, causes said medicine container unit (5*b*) to be closed with respect to said medicine storage chamber (5*a*) and causes said medicine container unit (5*b*) to be communicated with the exterior of the device through a pipe (2*g*, 2*d*);

means (13) operated from the outer side of the device to move said medicine guiding unit (2) between the filling position and the administering position; and a pump unit (3) capable of blowing air into said medicine container unit through a filter (6) provided in the bottom of said medicine container unit (5*b*);

wherein said medicine guiding unit (2), at the filling position, enables said medicine container unit (5*b*) to be filled with the powdered medicine from said medicine storage chamber (5*a*) through said opening means, sweeps and meters the powdery medicine in said medicine container unit (5*b*) into the amount of one time of administering operation as it moves from the filling position to the administering position, and, at the administering position, permits the powdery medicine in said medicine container unit (5*b*) to be injected out of the device together with the air through said pipe (2*g*, 2*d*, 2*c*) when said pump unit (3) is operated.

2. A powdered medicine multi-dose administering device according to claim 1, wherein said body (1) of the device is integrally molded using a resin.

3. A powdered medicine multi-dose administering device according to claim 1, wherein said medicine guiding unit (2) includes a lower disk-like portion and a pole-like portion extending upward from said disk-like portion, which are integrally molded together using a resin, said opening means (**2*f*) is so formed as to penetrate through the disk-like portion up and down, and said pipe (2*g*, 2*d*, 2*c*) is opened at its one end on the lower surface (2*e***) of the disk-like portion and is opened at its other end in the upper end of said pole-like portion.

4. A powdered medicine multi-dose administering device according to claim 3, wherein said device body (1) is nearly of a cylindrical shape, said disk-like portion of said medicine guiding unit (2) has a diameter smaller than the inner diameter of said medicine storage chamber (**5*a*) of said device body, and said medicine guiding unit (2**) is allowed to rotate between the filling position and the administering position over a predetermined angular range.

5. A powdered medicine multi-dose administering device according to claim 3, wherein said device body (1) has a closure unit (4) on the medicine storage unit (**5*a*), the closure unit has a shaft hole (11) at the center thereof for passing through the pole-like portion of said medicine guiding unit (2), and the medicine storage chamber (5*a*) is sealed with said closure unit, said medicine storage unit (5*a*) and said medicine guiding unit (2**).

6. A powdered medicine multi-dose administering device according to claim 5, wherein the bottom surface (**2*e*) of the disk-like portion of said medicine guiding unit (2) comes in contact with the bottom surface of the medicine storage chamber (5*a*), the upper and lower positions of said medicine guiding unit (2) are limited by a contact portion (10) formed on said pole-like portion so as to come into contact with the inner surface of said closure unit (4), and the bottom surface (2*e*) of the disk-like portion of said medicine guiding unit (2) is brought into intimate contact with the bottom surface of the medicine storage chamber (5*a***).

7. A powdered medicine multi-dose administering device according to claim 6, wherein said medicine guiding unit (2) has a shaft (**2*j*) of a circular shape in cross section formed in the upper part of said junction portion (10) of the pole-like portion so as to be fitted to the shaft hole (11) of said closure unit (4), and has a shaft (2*k*) of a non-circular shape in cross section formed in the upper part thereof, said means operated from the outside of the device to move the medicine guiding unit (2) between the filling position and the administering position, is a rotary spray metering change-over device (13) which has a non-circular hole (13*c*) that fits to the shaft (2*k*) of a non-circular shape in cross section of the pole portion of said medicine guiding unit (2), and said medicine guiding unit (2) moves between the filling position and the administering position being interlocked to the rotational operation of said change-over device (13**).

8. A powdered medicine multi-dose administering device according to claim 7, wherein said rotary spray metering change-over device (13) includes a cylindrical portion (**13*a*) having a large diameter and a cylindrical portion (13*b*) having a small diameter, that are molded integrally together using a resin, the outer periphery of the cylindrical portion having a large diameter forms a rotary operation portion, and the cylindrical portion of a small diameter defines a powdered medicine passage (2*c*) formed therein, has the non-circular hole (13*c*) formed in the base portion, and defines a spray port in an end (2*h***) thereof.

9. A powdered medicine multi-dose administering device according to claim 8, wherein said rotary spray metering change-over device (13) is formed to be detachable from said device body (1) and said medicine guiding unit (2).

10. A powdered medicine multi-dose administering device according to claim 3, wherein a central hole (14) is formed at the center in the bottom surface (**2*e*) of the disk-like portion of said medicine guiding unit (2), and a protuberance (8) is formed at the center on the bottom surface of said medicine storage chamber (5*a*) to work as a shaft that fits to the central hole (14) in order to stabilize the turn of the medicine guiding unit (2**).

11. A powdered medicine multi-dose administering device according to claim 4, wherein said medicine guiding unit (2) has an arcuate groove (12) formed in the bottom surface (**2*e*) of the disk-like portion with said central hole (14) as a center, said medicine storage unit (5*a*) has a protuberance (7) formed on the bottom surface thereof so as to be inserted in the arcuate groove thereby to limit the turning range of the medicine guiding unit (2) and of the rotary spray metering change-over device (13), wherein, when the protuberance (7) is located at an end of the arcuate groove (12**), the position for filling the powdered medicine is limited and, when the protuberance is located at the other end, the position for administering the powdered medicine is limited.

12. A powdered medicine multi-dose administering device according to claim 4 wherein, on the bottom surface of the disk-like portion of said medicine guiding unit (2), an angle (x) subtended by the center of said opening means (**2*f*) and the center of the opening of said pipe (2*g*) is equal to, or is slightly smaller than an angle ($\gamma$) subtended by one end and other end of the arcuate groove (12**) ($x \leqq y$), and lies in a range of 60 degrees to 180 degrees.

13. A powdered medicine multi-dose administering device according to claim 2, wherein said the disk-like portion of said medicine guiding unit (2) on the side of the medicine storage chamber (**5*a*) is inclined upward from the periphery toward the center at an angle ($\alpha$) in a range of from 15 degrees to 45 degrees with respect to the bottom surface (2*e***) of said disk-like portion.

14. A powdered medicine multi-dose administering device according to claim 2, wherein said pipe (**2*g*) provided in said medicine guiding unit (2) is inclined upward at angles ($\beta$, $\gamma$) in a range of from 20 degrees to 70 degrees with respect to the bottom surface (2*e*) of the medicine guiding unit (2**).

15. A powdered medicine multi-dose administering device according to claim 1, wherein said opening means (**2*f*) in said medicine guiding unit (2) is a hole (2*f***) penetrating through the disk-like portion up and down.

16. A powdered medicine multi-dose administering device according to claim 15, wherein said hole (**2*f*) is extending upward from the opening in the bottom surface (2*e*) of the disk-like portion, and is expanding on the side facing the medicine storage chamber (5*a*) toward the side of the opening of said pipe (2*g*) thereby to form a pocket-like dent (2*m*), the dent assisting a smooth conveyance of the powdered medicine in the medicine storage chamber (5*a*) into the medicine container chamber (5*b***) during the operation for changing over the filling and administering.

17. A powdered medicine multi-dose administering device according to claim 4, wherein one vane or plural pieces of vanes (21) are formed on the outer side of said pole-like portion of said medicine guiding unit (2), so that the powdered medicine in the medicine storage chamber (**5*a*) is stirred as the medicine guiding unit (2**) moves between the filling position and the administering position.

18. A powdered medicine multi-dose administering device according to claim 1, wherein said pump unit (3) is at least partly constituted by a flexible resin so as to define an air chamber therein, the opening portion of said pump unit (3) is coupled to the lower part of the device body (1), the pump unit (3) is depressed and relaxed to blow the air into the medicine container chamber (5*b*) through said filter (6) in the air chamber, and the powdered medicine is injected out of the device through said pipe (2*g*, 2*d*, 2*c*).

19. A powdered medicine multi-dose administering device according to claim 1, wherein said filter (6) has a recessed portion or a protruded portion on the side facing said medicine container chamber (5*b*) to adjust the volume of said medicine container chamber (5*b*).

20. A powdered medicine multi-dose administering device according to claim 1, wherein said medicine guiding unit (2) is obtained by molding one or more kinds of high-molecular materials selected from the group consisting of a polycarbonate, ABS, a high-impact polystyrene and a cyclic olefin copolymer.

21. A powdered medicine multi-dose administering device according to claim 1, wherein a drying agent is mounted on a portion of the device.

22. A powdered medicine multi-dose administering device according to claim 1, wherein said powdered medicine administering device is disposable.

23. A powdered medicine multi-dose administering device according to claim 1, wherein said powdered medicine administering device is for administering the medicine into the body cavity.

24. A powdered medicine multi-dose administering device according to claim 1, wherein said powdered medicine administering device is for administering the medicine into the nasal cavity.

25. A powdered medicine multi-dose administering device according to claim 1, wherein said powdered medicine administering device is for administering the medicine into the lungs.

26. A powdered medicine multi-dose administering method, wherein a stationary medicine container unit (5*b*) for containing a powdered medicine of a unit-dose amount is provided under the bottom surface of a stationary medicine storage chamber (5*a*) which is formed integrally with said medicine container unit (5*b*) to form a unitary body (1), a movable medicine guiding unit (2) is provided to move between a filling position and an administering position while maintaining a contact with the bottom surface of said medicine storage chamber (5*a*) so that, when moved to the filling position, said medicine container unit (5*b*) is opened to said medicine storage chamber (5*a*) through opening means (2*f*) and, when moved to the administering position, said medicine container unit (5*b*) is closed with respect to said medicine storage chamber (5*a*) and is communicated with the exterior of the device through a pipe (2*g*, 2*d*);

said medicine guiding unit (2) is moved between the filling position and the administering position, so that:

at the filling position, said medicine container unit (5*b*) is filled with the powdered medicine from said medicine storage chamber (5*a*) through said opening means;

the powdered medicine in said medicine container unit (5*b*) is swept and metered into the amount of one time of administering operation as said medicine guiding unit moves from the filling position to the administering position; and, at the administering position, a pump (3) is operated to blow air into said medicine container unit (5*b*) through the filter (6) to inject the powdered medicine out of the device through said pipes (2*g*, 2*d*, 2*c*).

* * * * *